United States Patent [19]

Rohr et al.

[11] 4,394,327
[45] Jul. 19, 1983

[54] HERBICIDALLY ACTIVE PHENOXY-α-PHENOXY-ALKANECARBOXYLIC ACID DERIVATIVES

[75] Inventors: Otto Rohr, Therwil, Switzerland; Georg Pissiotas, Lörrach, Fed. Rep. of Germany; Beat Böhner, Binningen; Kurt Burdeska, Basel, both of Switzerland

[73] Assignee: Ciba-Geigy Corporation, Ardsley, N.Y.

[21] Appl. No.: 263,650

[22] Filed: May 14, 1981

Related U.S. Application Data

[60] Division of Ser. No. 83,906, Oct. 11, 1979, abandoned, which is a continuation-in-part of Ser. No. 883,021, Mar. 3, 1978, abandoned.

[30] Foreign Application Priority Data

Mar. 8, 1977 [CH] Switzerland ........................ 2867/77
Jul. 4, 1977 [CH] Switzerland ........................ 8182/77

[51] Int. Cl.³ ................. C07C 153/07; C07C 121/75; A01N 41/00
[52] U.S. Cl. ........................... 260/455 R; 260/465 D; 71/100; 71/105
[58] Field of Search ...................... 260/455 R, 465 D; 71/105, 100

[56] References Cited

U.S. PATENT DOCUMENTS

| | | | |
|---|---|---|---|
| 2,412,510 | 12/1946 | Jones | 71/118 |
| 3,784,635 | 1/1974 | Theissen | 71/105 |
| 4,070,177 | 1/1978 | Nishiyama et al. | 71/105 |
| 4,070,178 | 1/1978 | Johnson et al. | 71/118 |
| 4,106,925 | 8/1978 | Rohr et al. | 71/105 |
| 4,134,753 | 1/1979 | Horlein et al. | 71/108 |

FOREIGN PATENT DOCUMENTS 2730591 1/1978 Fed. Rep. of Germany .
50-160427 12/1975 Japan .

Primary Examiner—Dolph H. Torrence
Attorney, Agent, or Firm—Frederick H. Rabin

[57] ABSTRACT

3-Phenoxy-α-phenoxy-alkanecarboxylic acid derivatives of the formula

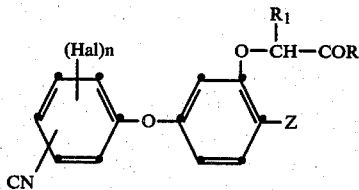

Wherein Hal is a halogen atom, n is an integer from 1 to 3, R is an acid function and Z is hydrogen or $C_1$–$C_4$ alkyl, are disclosed as possessing a surprising selective herbicidal activity. Methods are disclosed for combatting weeds in mono- and dicotyledonous cultures such as cereals, corn, rice, soya and cotton, which comprise applying to the locus to be protected from weeds a dosage of from 0.1 to 10.0 kilograms per hectare of the above compounds.

4 Claims, No Drawings

HERBICIDALLY ACTIVE PHENOXY-α-PHENOXY-ALKANECARBOXYLIC ACID DERIVATIVES

CROSS-REFERENCE TO RELATED APPLICATION

This is a division of application Ser. No. 083,906 filed on Oct. 11, 1979, which is a continuation-in part of application Ser. No. 883,021, filed on Mar. 3, 1978, now both abandoned.

DETAILED DISCLOSURE

The present application relates to a group of novel, herbicidally active substituted 3-phenoxy-α-phenoxy-alkanecarboxylic acid derivatives which have a substituent in the α-phenoxy radical in the para-position to the 3-phenoxy moiety, processes for their production, herbicidal compositions which contain these novel compounds as active ingredient, and to a method of selectively controlling weeds in crops of cultivated plants which comprises the use of these active ingredients or of compositions containing them.

The novel active compounds have the formula I

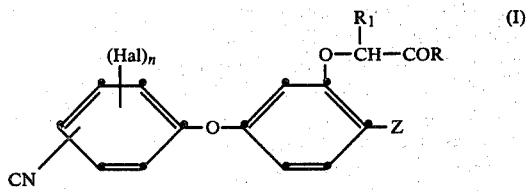

wherein

R is a radical $ON=C(R_2)_2$, $OR_3$, $SR_4$ or $NR_5R_6$,

Hal is a halogen atom, n is an integer 1, 2 or 3,

Z is a halogen atom or the cyano group, $R_1$ is hydrogen or $C_1$-$C_4$alkyl, $R_2$ is $C_1$-$C_4$alkyl or one $R_2$ is hydrogen, $R_3$ is hydrogen or the cation of a base $(1/n)M^{n\oplus}$, M is an alkali or alkaline earth metal cation or an iron, copper, zinc, manganese or nickel cation or an ammonio radical

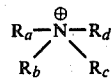

and n as an integer 1, 2 or 3 corresponds to the valency of the cation, while $R_a$, $R_b$, $R_c$ and $R_d$, each independently of the other, represent hydrogen, benzyl or a $C_1$-$C_4$alkyl radical which is unsubstituted or substituted by OH, $NH_2$ or $C_1$-$C_4$alkoxy, $R_3$ and $R_4$ are a $C_1$-$C_8$alkyl radical which is unsubstituted or substituted by halogen, cyano, $C_1$-$C_4$alkoxy, $C_1$-$C_4$alkylthio, $C_2$-$C_8$-alkoxycarbonyl, bis($C_1$-$C_4$alkyl)amino, $C_3$-$C_8$cycloalkyl, or cycloalkenyl, or also by a phenyl or phenoxy radical, which is unsubstituted or is mono- to trisubstituted by halogen, $C_1$-$C_4$alkyl or $C_1$-$C_4$alkoxy;

a $C_3$-$C_8$alkenyl or alkynyl radical which is unsubstituted or mono- to tetrasubstituted by halogen;

a $C_3$-$C_{12}$cycloalkyl or cycloalkenyl radical which is unsubstituted or substituted by halogen;

a phenyl radical which is unsubstituted or mono- to trisubstituted by halogen, $C_1$-$C_4$alkyl, $C_1$-$C_4$alkoxy, $C_1$-$C_4$alkylthio, nitro, cyano or trifluoromethyl;

$R_5$ and $R_6$ represent hydrogen or $C_1$-$C_6$alkyl which may be interrupted by oxygen or sulfur or substituted by halogen, cyano or hydroxyl; $C_2$-$C_6$alkenyl or alkynyl optionally substituted by halogen; $C_3$-$C_8$cycloalkyl or cycloalkenyl or $R_5$ and $R_6$ together with the nitrogen atom, to which they are attached can also form a heterocyclic ring with 5 to 6 ring members.

In the above formula, the alkyl radicals are both branched and unbranched and contain the indicated number of carbon atoms. The substituents $R_5$ and $R_6$ are preferably hydrogen or $C_1$-$C_4$alkyl radicals. However, individual alkyl radicals can also be cyclic preferably cyclopropyl or cyclohexyl or aromatic, e.g. a substituted or unsubstituted phenyl radical, araliphatic, like unsubstituted or substituted benzyl, or two alkyl radicals together with the nitrogen atom to which they are attached can also form a heterocyclic ring system which preferably contain 5 to 6 ring members.

Similar phenoxy-phenoxy-alkanecarboxylic acid derivatives which, however, carry the alkanecarboxylic acid radical in the para-position, are known from German Offenlegungsschriften Nos. 2,136,828, 2,223,894, 2,433,067 and 2,531,643.

These known compounds have a special action against grasses and are suitable for the selective control of grass-like weeds in crops of mono- and dicotyledonous plants. However, they have no action at all against dicotyledonous weeds, or are only effective if used in very high rates of applications.

The surprising discovery has now been made that the novel phenoxy-α-alkanecarboxylic acid derivatives of the formula I, which have the alkanecarboxylic acid radical in the meta-position, are highly suitable for controlling dicotyledonous weeds in crops of primarily monocotyledonous plants, such as cereals (e.g. wheat, barley, sorghum), maize, and also for controlling Sagittaria and Cyperus species in rice, as well as individually for selectively controlling weeds in crops of dicotyledonous plants, such as sugar beat, soya, and cotton.

A particularly good tolerance to rice—both hill rice and transplanted lowland rice—has been observed.

The compounds of the formula I are most effective against the following dicotyledonous weeds: *Sagittaria pygmea, Sinapis alba, Sida spinosa, Sesbania exaltata, Ipomoea purpurea, Galium aparine, Chrysantheaum leucum,* Abutilon, *Solanum nigrum, Ammonia indica, Rotala indica, Cyperus difformia, Elatine triandra, Lindernia procumbens* etc.

Although the novel compounds also have a good preemergent action, their postemergent action is especially effective and advantageous.

A number of the novel active compounds are also suitable for desiccation and defoliation in cotton and potato crops shortly before harvesting.

The rates of application of herbicide of the present invention per hectare vary, depending on the activity of the respective active substance, the nature of the soil, climatic and weather conditions, the nature and time of application and the type of crop and the weeds to be controlled, between 0.1 and 10 kg, preferably between 0.5 and 4 kg.

Particularly suitable compounds are those of the formulae

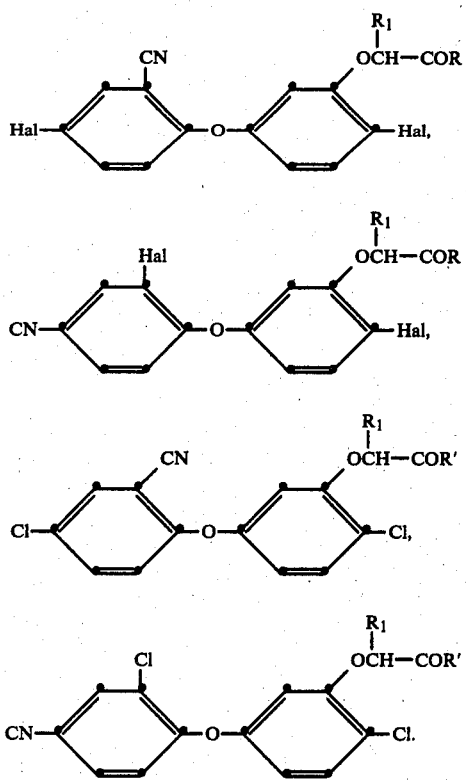

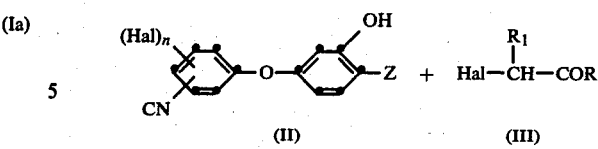

In these formulae Hal, R and $R_1$ have the meaning given above, while R' is a group $OR_3'$, $SR_4'$ or $NR_5R_6$, wherein $R_3'$ and $R_4'$ are $C_1$-$C_8$ alkyl unsubstituted or substituted by halogen, cyano or interrupted by oxygen, sulfur, a carbonyl or a carboxyloxy group; $C_2$-$C_8$ alkenyl or alkynyl, unsubstituted or substituted by halogen; $C_3$-$C_8$cycloalkyl or cycloalkenyl; phenyl or benzyl unsubstituted or substituted by halogen, cyano, nitro, $C_1$-$C_4$alkyl, alkoxy or by trifluoromethyl. $R_5$ and $R_6$ have the above given meaning.

Within the group of compounds of the formula I particularly interesting are:
3-(2'-chloro-4'-cyanophenoxy)-α-(6-chlorophenoxy)-propionic acid-methyl ester,
3-(2'-chloro-4'-cyanophenoxy)-α-(6-chlorophenoxy)-propionic acid-benzyl ester,
3-(2'-chloro-4'-cyanophenoxy)-α-(6-chlorophenoxy)-propionic acid-allyl ester,
3-(2'-cyano-4'-chlorophenoxy)-α-(6-chlorophenoxy)-propionic acid-methyl ester,
3-(2'-chloro-4'-cyanophenoxy)-α-(6-chlorophenoxy)-propionic acid-thiomethyl ester,
3-(2'-chloro-4'-cyanophenoxy)-α-(6-chlorophenoxy)-propionic acid-thioallyl ester,
3-(2'-chloro-4'-cyanophenoxy)-α-(6-chlorophenoxy)-propionic acid-thiobenzyl ester.

The novel compounds of the formula I are manufactured by the methods which are known per se for such syntheses.

The last step of the synthesis always consists of the following reaction step and constitutes the process of the present invention:

Accordingly, a start is made from a 3-hydroxy-diphenyl ether of the formula II, which is reacted with an α-halogen-alkanoic acid derivative or with a nitrile of the formula III in the presence of a base.

If a carboxylic acid (A=COOH) is used as starting material of the formula III in this process, then this group can subsequently be converted into another derivative of the formula I as defined herein, either direct or by way of the corresponding acid chloride.

If an ester of the formula III is used, the ester group can be converted by saponification into the free carboxylic acid, a salt thereof, and then into an amide.

In the formulae II and III of the starting materials, n and the symbols A, X, Y and Z are as defined in formula I and Hal represents a halogen atom, such as chlorine, bromine etc.

The above reaction can be carried out in the presence or absence of solvents or diluents which are inert to the reactants. Polar organic solvents, such as methyl ethyl ketone, dimethyl formamide, dimethyl sulphoxide etc., are preferred. The reaction temperatures are between 0° and 200° C., preferably between 20° and 100° C., and the reaction time is from 1 hour by several days, depending on the starting material, choice of reaction temperature, and the solvent. The process is usually carried out under normal pressure. Suitable bases (condensation agents) for the reaction are those customarily employed, for example KOH, $NaOCH_3$, $NaHCO_3$, $K_2CO_3$, potassium tert-butylate etc., and also organic bases, such as triethylamine.

The starting materials of the formula III are known or they can be prepared by conventional methods. Many starting phenols of the formula II are also already known.

Phenoxyphenols of the formula II which have not yet been described can be easily prepared by conventional methods and techniques, for example as described in German Offenlegungsschriften Nos. 2,433,066 and 2,433,067.

Accordingly, for example, 2-methoxy-4-chloro-nitrobenzene of the formula

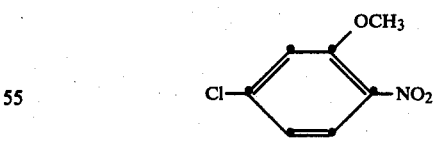

can be reacted with a phenol of the formula IV

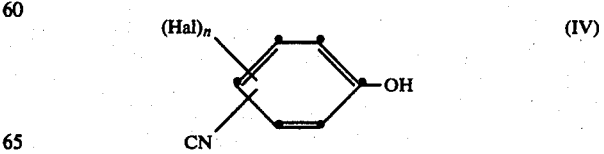

in an alkaline medium, to give the nitro compound of the formula V

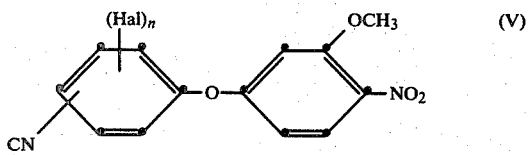

for example in accordance with the particulars of German Offenlegungsschrift No. 2,304,006.

The same nitro compound is also obtained by reaction of 2 moles of a phenol of the formula IV with 2,4-dichloronitrobenzene. In this reaction, a compound of the formula

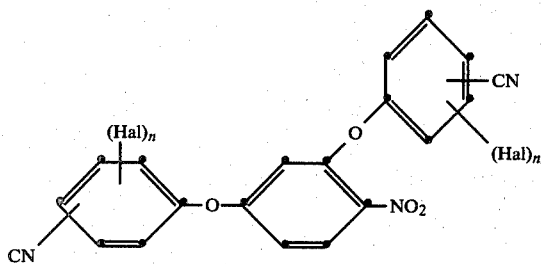

is formed as intermediate, which is then "transetherified" by heating with methanol and KOH in dioxane to give the methoxy compound V (method described in German Offenlegungsschrift No. 2,533,172).

The resulting nitrated intermediate V is reacted by a conventional reduction of the nitro group to give the corresponding amine, which is then converted into the diazonium salt (e.g. diazonium chloride). Finally, the diazo group of the diazonium salt is replaced by conventional methods by the cyano group or by a halogen atom.

The reduction of the nitro group in V is carried out catalytically with hydrogen (for example with Raney nickel) in solution in an inert solvent, or by gradual addition of V to a mixture of iron powder and dilute hydrochloric acid at elevated temperature.

The diazotisation of the resulting amine is effected in conventional manner in solution in dilute hydrochloric acid by the dropwise addition of an aqueous $NaNO_2$ solution at temperatures below 5° C.

The substitution of the cyano group for the diazo group is carried out by the dropwise addition of the disodium salt to an aqueous solution of $K_3[Cu(CN)_4]$ or by the addition of copper powder and copper (I) cyanide to the solution of the diazonium salt. These reactions to give p-cyano-diphenyl-ethers, starting from substituted p-nitro-diphenyl ethers have already been described in German Offenlegungsschrift No. 1,912,600.

The substitution of chlorine for the diazo group is effected by addition of copper (I) chloride (CuCl) and finely divided copper powder to the diazonium chloride solution.

The substitution of bromide for the diazo group is best effected by addition of KBr and CuBr to a diazonium salt solution, whilst the substitution of iodine for the diazo group can be carried out by treating diazonium salt with potassium iodide.

The halogen atom represented by Z can also be obtained by halogenating the diphenyl ether which is unsubstituted in the 4'-position.

In order finally to obtain the corresponding free starting phenol of the formula II from the compounds prepared in the manner described above, the ether protective group in the meta-position (—O—CH₃) is cleaved, for example with HBr in glacial acetic acid.

The production of a number of phenoxy-phenoxy-alkanecarboxylic acid derivatives of the formula I is illustrated in the following Examples. Further active compounds obtained in corresponding manner are listed in the subsequent table.

Temperatures are given therein in degrees Centigrades. The parts and percentages are by weight. Pressures are given in Torricelli (torr) or mm Hg (=1.333 millibar).

EXAMPLE 1

3-(2',4'-Dichlorophenoxy)-α-(6-cyanophenoxy)-propionic acid methyl ester (a) 56.8 g of 2,4-dichloro-3'-methoxy-4'-amino-diphenyl ether in 240 ml of water are charged into a 1.5 liter sulphonating flask. Then 123 g of conc. sulphuric acid are slowly added, whereupon the temperature rises to 75° C. and a solution is formed. After cooling, the sulphate precipitates in the form of a dense crystal slurry, which is diluted with 200 ml of ice-water. The slurry, which is cooled to 0°-5° C., is diazotised in the course of about 30 minutes with 66 ml of 20% nitrite solution. After stirring for 1 hour, a solution of 36 g of potassium iodide in 55 ml of water is added, and after a short time a just barely stirrable mass forms, which is diluted with 300 ml of toluene. After stirring overnight, the organic phase is separated and the solvent distilled off, affording 75 g of 2,4-dichloro-3'-methoxy-4'-iodo-diphenyl ether in the form of a dark oil, which is distilled in a high vacuum. Boiling point: 174°-180° C. at 0.3 torr.

(b) 63 g of the above 2,4-dichloro-3'-methoxy-4'-iodo-diphenyl ether in 135 ml of N-methyl-2-pyrrolidone are charged into a 500 ml sulphonating flask. With good stirring, 16.9 g of copper (I) cyanide are added slowly. The reaction mixture is heated to 140° C. bath temperature under a weak flow of nitrogen and stirred for 3 hours at this temperature. The reaction mixture is then cooled to room temperature and copper (I) iodide is filtered off. The filtrate is stirred into a mixture of 270 g of ice and 90 ml of ammonia solution (25%). The precipitate is collected by filtration and recrystallised from alcohol/water, affording 46.5 g of 2,4-dichloro-3'-methoxy-4'-cyano-diphenyl ether.

(c) 15 g of the above diphenyl ether are dissolved in 80 ml of acetic anhydride and 185 ml of glacial acetic acid and, after addition of 36 ml of 57% hydroiodic acid, the reaction mixture is stirred for 24 hours under nitrogen at 120° C. bath temperature. The solvent is then distilled off by rotary evaporation and the residual oily product is extracted with toluene, affording 14 g of 2,4-dichloro-3'-hydroxy-4'-cyano-diphenyl ether in the form of a highly viscous oil.

(d) 14 g of the above phenol are reacted, as described in (c), with methyl 2-bromopropionate. The crude oil obtained is purified over alumina, affording 10 g of 3-(2',4'-dichlorophenoxy)-α-(6-cyanophenoxy)-propionic acid methyl ester with a refractive idex $n_D^{23} = 1.5532$.

EXAMPLE 2

3-(2'-Cyano-4'-chlorophenoxy)-α-(6-chlorophenoxy)-propionic acid methyl ester (a) 66 g of resorcinol are added to 220 ml of dimethyl sulphoxide. With stirring, 37.4 g of potassium hydroxide (powder) are added, whereupon the temperature rises to 55° C. The mixture is kept for 30 minutes at 60° C. and the 51.6 g of 2,5-dichlorobenzonitrile are added in portions. The reaction mixture is then stirred for 7 hours at 90° C. and, after cooling, poured into ice-water. The pH is adjusted to 6 with conc. hydrochloric acid and initially a brown oil precipitates, which soon becomes crystalline. Crystallisation from ethanol/-water yields 49.6 g of 3-(2'-cyano-4'-chlorophenoxy)-phenol with a melting point of 118°–120° C.

(b) 40 g of the above 3-(2'-cyano-4'-chlorophenoxy)-phenol and 24.8 ml of triethylamine are added to 200 ml of tetrahydrofurane. With stirring, 12.2 ml of acetyl chloride are added dropwise while cooling with an ice bath. The reaction mixture is then stirred for 8 hours at room temperature and filtered. The filtrate is concentrated in vacuo, affording 45 g of 3-acetoxy-2'-cyano-4'-chloro-diphenyl ether. Melting point: 64.5° C.

(c) 10 g of the above 3-acetoxy-2'-cyano-4'-chloro-diphenyl ether are added to 100 ml of acetic acid. At 20° C. chlorine is introduced until no more starting material can be detected by gas chromatography. The reaction mixture is concentrated and the residue distilled in a high vacuum, affording 7 g of 3-acetoxy-2'-cyano-4,4'-dichlorodiphenyl ether. Boiling point: 174° C./0.05 mm.

(d) Saponification of the above acetate with NaOH in water/ethanol at reflux yields 3-hydroxy-2'-cyano-4,4'-dichloro-diphenyl ether, which precipitates on cooling. Melting point: 132° C.

(e) 60 g of 3-hydroxy-2'-cyano-4,4'-dichloro-diphenyl ether and 24 ml of methyl 2-bromopropionate are stirred overnight at 100° C. (bath temperature) in 600 ml of ethyl methyl ketone with 29.6 g of potassium carbonate. After removing inorganic salts by filtration, the filtrate is concentrated to dryness. The crystalline mass is recrystallised from methanol, affording 81.7 g of 3-(2'-cyano-4'-chlorophenoxy)-α-(6-chlorophenoxy)-propionic acid methyl ester with a melting point of 105° C.

Further to these examples, the following compounds were prepared:

3-(2'-chloro-4'-cyanophenoxy)-α-(6-chlorophenoxy)-propionic acid-methyl ester, b.p.>200°/0.001 torr and the compounds of the following Table.

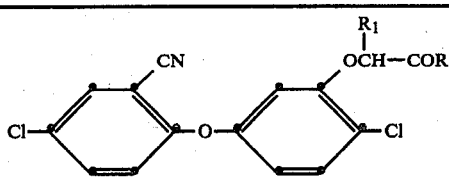

| Compound No. | $R_1$ | R | Physical constant |
|---|---|---|---|
| 1 | $CH_3$ | $OCH_3$ | b.p. 104–5°/0.01 torr |
| 2 | $C_2H_5$ | $OC_2H_5$ | oil |
| 3 | $CH_3$ | $OC_4H_9sec$ | oil |
| 4 | $CH_3$ | $OC_4H_9iso$ | oil |
| 5 | $CH_3$ | $OC_4H_9n$ | oil |
| 6 | $CH_3$ | $OC_3H_7n$ | oil |
| 7 | $CH_3$ | $OC_3H_7iso$ | oil |
| 8 | $CH_3$ | $OCH_2COOCH_3$ | m.p. 105–8° |
| 9 | $CH_3$ | $OCH_2COOC_2H_5$ | m.p. 65–67° |
| 10 | $CH_3$ | $OCH_2CH(CH_3)C_2H_5$ | oil |
| 11 | $CH_3$ | $OCH_2\text{-}\langle\text{cyclopropyl}\rangle$ | m.p. 121–122° |
| 12 | $CH_3$ | OH | m.p. 135–6° |
| 13 | $CH_3$ | $OCH_2-C\equiv CH$ | oil |
| 14 | $CH_3$ | $OCH_2-CH=CH_2$ | oil |
| 15 | $CH_3$ | $SCH_3$ | m.p. 79–80° |
| 16 | $CH_3$ | $SC_2H_5$ | m.p. 68–69° |
| 17 | $CH_3$ | $SCH_2\text{-}\langle\text{cyclopropyl}\rangle$ | $n_D^{23}$ 1-6110 |
| 18 | $CH_3$ | $SCH_2-CH=CH_2$ | oil |

The novel active substances of the formula I are stable compounds which are soluble in conventional organic solvents, such as alcohols, ethers, ketones, dimethyl formamide, dimethyl sulphoxide etc.

The compositions of the present invention are obtained in known manner by intimately mixing and grinding active substances of the general formula I with suitable carriers and/or additives, with or without the addition of antifoam agents, wetting agents, dispersants and/or solvents which are inert to the active substances. The active substances can be processed to the following formulations: solid formulations:

dusts, tracking powders, granules (coated granules, impregnated granules and homogeneous granules); active substance concentrates which are dispersible in water:

wettable powders, pastes, emulsions, emulsion concentrates; liquid formulations: solutions.

The concentrations of active substance in the compositions of this invention are between 1 and 80 percent by weight. As circumstances may require, the active substances can also be applied in low concentrations of about 0.05 to 1 percent by weight.

The compositions of the present invention can be mixed with other biocidal active substances or compositions. Thus in addition to containing the cited compounds of the formula I, the compositions of the present invention can also contain, for example, insecticides, fungicides, bactericides, fungistatic agents, bacteriostatic agents, nematocides or further herbicides, in order to broaden the activity spectrum.

Granules

The following substances are used to prepare 5% granules:
5 parts of one of the active substances of the formula I,
0.25 parts of epichlorohydrin,
0.25 parts of cetyl polyglycol ether,
3.50 parts of polyethylene glycol,
91 parts of kaolin (particle size 0.3–0.8 mm).

The active substance is mixed with epichlorohydrin and dissolved with 6 parts of acetone, and the polyethylene glycol and cetyl polyglycol ether are then added. The resultant solution is sprayed on kaolin and subsequently evaporated in vacuo.

Wettable Powder

The following constituents are used to prepare (a) a 70% and (b) a 10% wettable powder:

(a)
- 70 parts of 3-(4'-cyano-2'-chlorophenoxy)-α-(6-chlorophenoxy)-propionic acid methyl ester,
- 5 parts of sodium dibutylnaphthalene sulphate,
- 3 parts of naphthalenesulphonic acid/phenolsulphonic acid/formaldehyde condensate (3:2:1),
- 10 parts of kaolin,
- 12 parts of Champagne chalk;

(b)
- 10 parts of 3-(2'-dichlorophenoxy)-α-(6-chlorophenoxy)-propionic acid methyl ester,
- 3 parts of a mixture of the sodium salts of saturated fatty alcohol sulphates,
- 5 parts of naphthalenesulphonic acid/formaldehyde condensate,
- 82 parts of kaolin.

The respective active substance is applied to the corresponding carriers (kaolin and chalk) and then these are mixed and ground, to yield wettable powders and excellent wettability and suspension powder. By diluting these wettable powders with water it is possible to obtain suspensions containing 0.1 to 80% of active substance. These suspensions are suitable for controlling weeds in cultivations of plants.

Paste

The following substances are used to prepare a 45% paste:
- 45 parts of 3-(2'-chloro-4'-cyano-phenoxy)-α-(6-chlorophenoxy)-propionic acid methyl ester or one of the other cited active compounds of the formula I,
- 5 parts of sodium aluminium silicate,
- 14 parts of cetyl polyglycol ether with 8 moles of ethylene oxide,
- 1 parts of oleyl polyglycol ether with 5 moles of ethylene oxide,
- 2 parts of spindle oil,
- 10 parts of polyethylene glycol,
- 23 parts of water.

The active substance is intimately mixed with the additives in appropriate devices and ground. A paste is obtained from which, by dilution with water, it is possible to manufacture suspensions of the desired concentration of active substance.

Emulsifiable Concentrate

The following ingredients are mixed to prepare 25% emulsion concentrate:
- 25 parts of 3-(2'-chloro-4'-cyano-phenoxy)-α-(6-chlorophenoxy)-propionic acid methyl ester or one of the other cited active compounds of the formula I,
- 5 parts of a mixture of nonylphenolpolyoxyethylene and calcium dodecylbenzenesulphonate,
- 15 parts of cyclohexanone,
- 55 parts of xylene.

This concentrate can be diluted with water to give emulsions in suitable concentrations of e.g. 0.1 to 10%. Such emulsions are suitable for controlling weeds in cultivations of plants.

The novel 3-phenoxy-α-phenoxyalkanecarboxylic acid derivatives of the formula I and the compositions which contain them have an excellent selective herbicidal action against grass-like weeds in different crops of cultivated plants, and in addition they exert a plant growth regulating action.

A particularly preferred field of use in the selective control of chiefly, dicotyledonous weeds in cereal crops and, in addition, of Sagitaria and Cyperus species in rice. The dihalogenophenoxy-phenoxy-alkanecarboxylic acid derivatives, in particular dihalogenophenoxy-phenoxy-propionic acid derivatives, of the formula I, have proved to be most effective.

Although the novel active substances of the formula I are effective in pre- and post-emergent application, the post-emergent application as contact herbicide is preferred although the pre-emergent use is also of interest.

The novel active compounds of the formula I, formulated for example a 25% wettable powders or for example, as emulsifiable concentrates, and diluted with water, are preferably applied to the crops of plants in the post-emergent stage.

Herbicidal action on applying the active compounds after emergence of the plants (post-emergent application)

Different cultivated plants and grass-like weeds are reared from seeds in pots in a greenhouse until they have reached the 4- to 6-leaf stage. Then the plants are sprayed with aqueous active substance emulsions (obtained from a 20% emulsifiable concentrate) in different rates of application. The treated plants are then kept at optimum light, watering, temperature (22°-25° C.) and humidity (50-70% relative humidity) conditions. Evaluation of the test was made 15 days after treatment. The state of the plants is examined and rated.

Almost all the tested compounds of formula I severely damaged the dicotyledonous plants and weeds, whereas monocotyledonous cultures were largely unharmed and the grass-like weeds suffered only slight to medium-severe damage.

Selective herbicidal action on rice in the post-emergent procedure

Twenty-five-day-old rice plants are transplanted into large rectangular asbestos cement containers in a greenhouse. Seeds of the weeds occurring in rice crops, namely *Echinochloa crus galli, Sagittaria pygm., Cyperus difformis, Ammania indica, Rotala indica, Elantine trianda* and *Lindernia procumbene*, are then sown between the rows of rice plants. The containers are well watered and kept at a temperature of about 25° C. and at high humidity. Twelve days later, when the weeds have emerged and reached the 2-3 leaf stage, the soil in each of the containers is covered with a layer of water to a height of 2.5 cm. The active substance is then applied in the form of an emulsion concentrate with a pipette, or else in granule from, between the rows of plants. The emulsifiable concentrate is diluted and applied so that it corresponds to a field application rate of 4, 2, 1 and 0.5 kg respectively of active substance per hectare. The test is evaluated 4 weeks later. In this test, compound 1 caused preciable damage to the weeds *Ammania indica, Rotala indica,* Lindernia, Elatine, Cyperus and Sagittaria. *Echinochloa crus gallia* was damaged merely slightly. The rice remained undamaged.

Desiccation and defoliation action

Cotton plants of the variety Deltapine were reared in earthenware pots in a greenhouse. After the first capsules had formed, the plants were sprayed with aqueous compositions of an active substance in a rate of application corresponding to 2, 0.6 and 0.3 kg/ha respectively in field application. Untreated plants served as controls. The evaluation of the test was made 3, 7 and 14 days after application of the active substance by determining the degree of defoliation (percentage of fallen leaves) and of desiccation (drying out of the leaves remaining on the plant).

Most of the tested compounds of formula I tested left only a few dried leaves on the plant.

What we claim is:

1. A compound of the formula

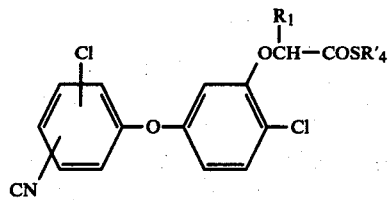

wherein
the floating substituents Cl and CN are in the 2- and 4-positions,
$R_1$ is hydrogen or $C_1$–$C_4$ alkyl, and
$R_4'$ is $C_1$–$C_8$ alkyl unsubstituted or substituted by halogen or cyano or interrupted by oxygen, sulfur, a carbonyl or a carboxyl oxy group; $C_2$–$C_8$ alkenyl optionally substituted by halogen; $C_2$–$C_8$ alkinyl optionally substituted by halogen; $C_3$–$C_8$ cycloalkyl; $C_3$–$C_8$ cycloalkenyl; phenyl unsubstituted or substituted by halogen, cyano, nitro, $C_2$–$C_4$ alkyl, $C_1$–$C_4$ alkoxy or trifluoromethyl; or benzyl unsubstituted or substituted by halogen, cyano, nitro, $C_1$–$C_4$ alkyl, $C_1$–$C_4$ alkoxy or trifluoromethyl.

2. The compound according to claim 1 which is 3-(2'-chloro-4'-cyanophenoxy)-α-(6-chlorophenoxy)-propionic acid thiomethyl ester.

3. The compound according to claim 1 which is 3-(2'-chloro-4'-cyanophenoxy)-α-(6-chlorophenoxy)-propionic acid thioallyl ester.

4. The compound according to claim 1 which is 3-(2'-chloro-4'-cyanophenoxy)-α-(6-chlorophenoxy)-propionic acid thiobenzyl ester.

* * * * *